United States Patent
Passaniti et al.

(10) Patent No.: US 11,698,355 B2
(45) Date of Patent: Jul. 11, 2023

(54) METHOD OF OPERATING A GAS SENSING DEVICE, AND CORRESPONDING GAS SENSING DEVICE

(71) Applicant: STMICROELECTRONICS S.r.l., Agrate Brianza (IT)

(72) Inventors: Fabio Passaniti, Syracuse (IT); Enrico Rosario Alessi, Catania (IT)

(73) Assignee: STMICROELECTRONICS S.r.l., Agrate Brianza (IT)

(*) Notice: Subject to any disclaimer, the term of this patent is extended or adjusted under 35 U.S.C. 154(b) by 353 days.

(21) Appl. No.: 16/917,285

(22) Filed: Jun. 30, 2020

(65) Prior Publication Data
US 2021/0003524 A1  Jan. 7, 2021

(30) Foreign Application Priority Data

Jul. 2, 2019  (IT) .................. 102019000010647

(51) Int. Cl.
*G01N 27/04* (2006.01)
*G01N 33/00* (2006.01)

(52) U.S. Cl.
CPC ....... *G01N 27/045* (2013.01); *G01N 33/0031* (2013.01); *G01N 33/0063* (2013.01)

(58) Field of Classification Search
USPC .................................................. 73/31.05
See application file for complete search history.

(56) References Cited

U.S. PATENT DOCUMENTS

| 4,219,806 A * | 8/1980 | Enemark ............ G01N 33/0063 422/96 |
| 5,356,756 A * | 10/1994 | Cavicchi ................ G01N 27/18 430/315 |
| 6,596,236 B2 * | 7/2003 | DiMeo, Jr. ............. G01N 21/59 73/31.06 |
| 10,067,048 B2 * | 9/2018 | Tiefenbach .......... G01N 27/045 |

(Continued)

FOREIGN PATENT DOCUMENTS

| CA | 3028548 A1 * | 1/2018 | ........... G01N 27/301 |
| CN | 108181350 A * | 6/2018 | ............. G01N 27/00 |

(Continued)

OTHER PUBLICATIONS

Gardner et al., "51 .1 : CMOS Gas Sensors and Smart Devices," *Proceedings of IEEE Sensors*, Jun. 12-14, 2002, Orlando, Florida, pp. 721-726.

*Primary Examiner* — Clayton E. LaBalle
*Assistant Examiner* — Warren K Fenwick
(74) *Attorney, Agent, or Firm* — Seed Intellectual Property Law Group LLP (57) ABSTRACT

A method of operating a gas sensing device is described. The method includes receiving a signal indicative of a value of resistance of a gas sensing element, processing the signal received to compute a value of a gas concentration, performing a comparison of the value of gas concentration to a threshold, and, based on the outcome of a diagnosis procedure, setting the device to an alert signal issue state as a function of the outcome of the comparison. The diagnosis procedure includes computing a set of parameters indicative of the state of the gas sensor circuit, and classifying the gas sensor circuit in one of a first, a second and a third class based on the parameters.

21 Claims, 4 Drawing Sheets

(56) References Cited

U.S. PATENT DOCUMENTS

| | | | | |
|---|---|---|---|---|
| 2002/0017126 A1* | 2/2002 | DiMeo, Jr. | ........... | G01N 27/128 |
| | | | | 73/31.05 |
| 2003/0153088 A1* | 8/2003 | DiMeo, Jr. | ........... | G01N 21/783 |
| | | | | 73/31.05 |
| 2006/0289400 A1* | 12/2006 | Takahashi | .............. | G01N 27/16 |
| | | | | 219/121.36 |

FOREIGN PATENT DOCUMENTS

| | | | | | |
|---|---|---|---|---|---|
| GB | 2311616 | A | | 10/1997 | |
| GB | 2 435 099 | A | | 8/2007 | |
| GB | 2435099 | A | * | 8/2007 | ........... B60K 28/063 |
| JP | H10143781 | A | * | 5/1998 | |
| JP | 2004197963 | A | * | 7/2004 | |
| JP | 3630512 | B2 | * | 3/2005 | |
| JP | 3860896 | B2 | * | 12/2006 | ........... G01N 27/419 |
| WO | 95/30144 | A1 | | 11/1995 | |
| WO | 2017/070819 | A1 | | 5/2017 | |

* cited by examiner

METHOD OF OPERATING A GAS SENSING DEVICE, AND CORRESPONDING GAS SENSING DEVICE

BACKGROUND

Technical Field

The description relates to gas sensors, such as MEMS metal oxide (MOX) gas sensors.

Description of the Related Art

Gas sensors have been playing a significant role in the development of personal and/or industrial electronic devices.

For instance, gas sensors with small size, low power consumption, ease of integration, high degree of functionality and good performance may facilitate the implementation of innovative functions in smart phones, personal electronic devices, medical consumer applications and the like. Gas sensors may also be involved in life-critical applications such as, e.g., air-bags, biosensors, aerospace devices and the like.

In particular, accuracy and stability over time of MEMS metal oxide gas sensors have been increasing in recent years, thereby facilitating application of this kind of sensors also in critical and/or harsh environments.

However, gas sensors may suffer from performance degradation over time, e.g., the operation state of the sensor may be affected by contamination and/or poisoning effects, aging effects, clogged holes, and other causes. Therefore, checking the operation state of a gas sensor (e.g., periodically) may be beneficial to avoid malfunctions of the sensor itself, e.g., detection of false positives and/or false negatives (e.g., missed detections). Also the response time of the gas sensor may be affected by contamination effects, poisoning effects, aging effects, etc.

Checking the operation state of a gas sensor (e.g., verifying its ability to correctly sense gas concentrations in the environment) may be a challenging issue.

At present, some MEMS gas sensor may involve periodic performance verification and, if necessary, re-calibration as a result of performance degradation being detected.

Conventionally, verification of the performance of a MEMS gas sensor may involve computing the accuracy error of the sensor over time by comparing the output of the sensor under test with the output of a reference professional instrument, e.g., at regular time intervals. In case the accuracy error is detected to have increased since a previous verification, or is detected to be out of specifications, re-calibration of sensor offset and/or sensor gain may be performed, e.g., by using a dedicated software or interface that runs on a microcontroller which controls operation of the sensor.

Additionally or alternatively, some high-end MEMS gas sensors may include built-in mechanisms for providing improved robustness and self-diagnosis capabilities, as well as compensation of performance degradation over time (often due to contaminants, poisoning effects or aging effects).

BRIEF SUMMARY

The disclosure provides improved self-diagnosis methods of gas sensors.

One or more embodiments may relate to methods of performing a self-diagnosis procedure for checking the operation state of a gas sensor. One or more embodiments may relate to a corresponding gas sensing device.

One or more embodiments may provide a method of operating a gas sensing device, wherein the gas sensing device may comprise a gas sensor circuit comprising a resistive gas sensing element, and a control circuit coupled to the gas sensor circuit, the method comprising:
receiving at the control circuit a signal from the gas sensor circuit, said signal being indicative of a value of resistance of said resistive gas sensing element;
processing said signal received from the gas sensor circuit to compute a value of a gas concentration;
performing a comparison of said value of gas concentration to a threshold value and setting the gas sensing device to an alert signal issue state as a function of the outcome of said comparison, wherein setting the gas sensing device to said alert signal issue state is conditioned on the outcome of a diagnosis procedure comprising:
computing a set of parameters indicative of the state of the gas sensor circuit;
classifying the gas sensor circuit as a function of the parameters in said set of parameters computed, in one of a first class, a second class and a third class indicative of the gas sensor circuit being faulty, degraded or correctly operating, respectively; and
i) as a result of the gas sensor circuit being classified in said first class, disabling setting the gas sensing device to said alert signal issue state;
ii) as a result of the gas sensor circuit being classified in said second class, triggering a sensitivity correction procedure of the gas sensor circuit and repeating said diagnosis procedure; and
iii) as a result of the gas sensor circuit being classified in said third class, enabling setting the gas sensing device to said alert signal issue state.

In some aspects, the disclosure includes a method of operating a gas sensing device, the method comprising: receiving a first signal from a gas sensor circuit having a resistive gas sensing element, the first signal being indicative of a resistance value of the resistive gas sensing element; processing the first signal to compute a value of a gas concentration; comparing the value of gas concentration to a threshold value; and setting the gas sensing device to an alert signal issue state based on an outcome of the comparing, wherein the setting the gas sensing device to the alert signal issue state includes a diagnosis procedure. The diagnosis procedure includes: computing a set of parameters indicative of a state of the gas sensor circuit; classifying the gas sensor circuit, based on values of the parameters in the set of parameters computed, in one of a first class, a second class and a third class indicative of the gas sensor circuit being faulty, degraded, or correctly operating, respectively; and i) in response to the gas sensor circuit being classified in the first class, disabling the setting the gas sensing device to the alert signal issue state; ii) in response to the gas sensor circuit being classified in the second class, triggering a sensitivity correction procedure of the gas sensor circuit; and iii) in response to the gas sensor circuit being classified in the third class, enabling setting the gas sensing device to the alert signal issue state.

The foregoing and other described aspects can each, include one or more of the following features:

A first feature, combinable with any of the previous or following features, specifies that the method comprises, as a result of the gas sensor circuit being classified in the first class, issuing a sensor fault signal.

A second feature, combinable with any of the previous or following features, specifies that the gas sensor circuit comprises a resistive heater, and wherein the sensitivity correction procedure comprises increasing a power supplied to the resistive heater.

A third feature, combinable with any of the previous or following features, specifies that the diagnosis procedure comprises: counting a number of consecutive executions of the sensitivity correction procedure; and classifying the gas sensor circuit in the first class as a result of the number of consecutive executions of the sensitivity correction procedure being higher than a threshold.

A fourth feature, combinable with any of the previous or following features, specifies that the computing the set of parameters comprises determining whether the values of the parameters in the set of parameters are in a steady state condition, and repeating the computing in response to the values of the parameters in the set of parameters failing to be in a steady state condition.

A fifth feature, combinable with any of the previous or following features, specifies that the classifying the gas sensor circuit based on the values of the parameters in the set of parameters comprises analyzing one or more of a time evolution pattern or a final value reached by a parameter in the set of parameters.

A sixth feature, combinable with any of the previous or following features, specifies that the gas sensor circuit comprises a resistive heater, and wherein the computing the set of parameters comprises: applying a current pulse to the resistive heater; sensing a second signal from the gas sensor circuit in response to the application of the current pulse; and computing, based on the second signal, a value of resistance of the resistive gas sensing element and a value of a slope of the second signal received.

A seventh feature, combinable with any of the previous or following features, specifies that the current pulse applied to the resistive heater comprises: a first portion having a first duration and a first current value; a second portion having a second duration and a second current value different from the first current value; and a third portion having a third duration and zero current value.

An eighth feature, combinable with any of the previous or following features, specifies that the first current value is higher than the second current value and the third duration is larger than each one of the first duration or the second duration.

A ninth feature, combinable with any of the previous or following features, specifies that the method comprises performing the diagnosis procedure at power-up of the gas sensing device.

A tenth feature, combinable with any of the previous or following features, specifies that the method comprises performing the diagnosis procedure after an alert signal is issued.

An eleventh feature, combinable with any of the previous or following features, specifies that the method comprises performing the diagnosis procedure periodically.

In some aspects, the disclosure includes a gas sensing device, comprising: a gas sensor circuit comprising a resistive gas sensing element; and a control circuit coupled to the gas sensor circuit. The control circuit is operable to control the gas sensor circuit by: applying a first signal on the gas sensor circuit; detecting a change of resistive value of the resistive sensing element in response to the first signal; determining an operation state of the gas sensor circuit based on the change of resistive value; and triggering a sensitivity correction procedure of the gas sensor circuit based on the operation state of the gas sensor.

A twelfth feature, combinable with any of the previous or following features, specifies that the control circuit is operable to control the gas sensor circuit based on the operation state of the gas sensor by: disabling the gas sensing device to issue an alert signal according to a measurement result of the gas sensor circuit; and enabling the gas sensing device to issue the alert signal according to the measurement result of the gas sensor circuit.

A thirteenth feature, combinable with any of the previous or following features, specifies that the gas sensor circuit comprises a resistive heater, and wherein the applying a first signal on the gas sensor circuit includes applying a current pulse to the resistive heater.

A fourteenth feature, combinable with any of the previous or following features, specifies that the detecting the change of resistive value of the resistive sensing element includes: sensing a second signal from the gas sensor circuit in response to the application of the current pulse; and computing, based on the second signal, a resistance value of the resistive gas sensing element and a slope of the change of the resistive value.

A fifteenth feature, combinable with any of the previous or following features, specifies that the current pulse includes: a first portion having a first duration and a first current value; a second portion having a second duration and a second current value different from the first current value; and a third portion having a third duration and zero current value.

A sixteenth feature, combinable with any of the previous or following features, specifies that the first current value is higher than the second current value and the third duration is larger than each one of the first duration or the second duration.

In some aspects, the disclosure includes a method, comprising: applying a current pulse on a MEMS gas sensor circuit having a resistive sensing element, the current pulse having a first stage and a second stage of different durations and different current values; detecting a change of resistive value of the resistive sensing element in response to the current pulse; determining a set of characteristics of the change of resistive value; and determining an operation state of the gas sensor circuit based on the set of characteristics.

A seventeenth feature, combinable with any of the previous or following features, specifies that the set of characteristics include a time evolution pattern of the change of resistive value and a resistive value of resistive sensing element at an end of the current pulse.

Advantageously over known solutions, one or more embodiments may not involve interrupting or stopping the operation of the tool or equipment where a gas sensor is installed in order to perform a self-diagnosis procedure of the gas sensor. In one or more embodiments, a self-diagnosis procedure may be carried out independently from the current operating conditions (e.g., environmental conditions) of the tool or equipment where the gas sensor is installed.

BRIEF DESCRIPTION OF THE SEVERAL VIEWS OF THE DRAWINGS

One or more embodiments will now be described, by way of example only, with reference to the figures, wherein.

DETAILED DESCRIPTION

In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments.

Throughout the figures annexed herein, like parts or elements are indicated with like references/numerals and a corresponding description will not be repeated for brevity.

The references used herein are provided merely for convenience and hence do not define the extent of protection or the scope of the embodiments.

Figure 1:
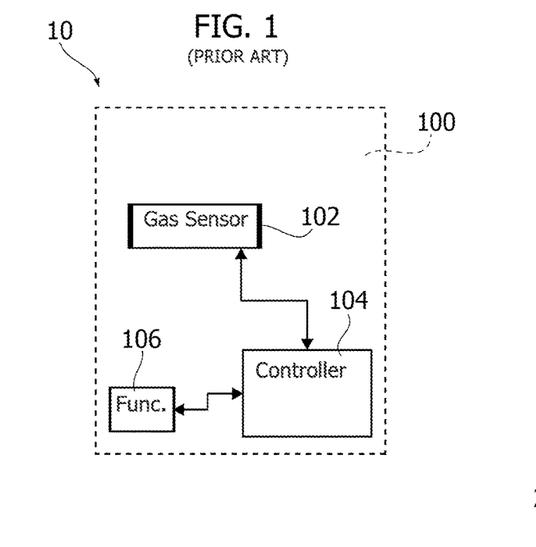
FIG. 1 is a system block diagram of an example gas sensing device.
Figure 2:
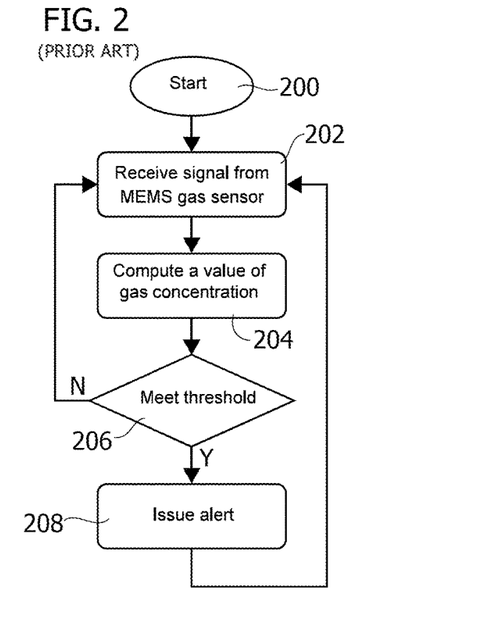
FIG. 2 is a flow diagram of an example operation flow of a conventional gas sensing device.

By way of general introduction to the detailed description of exemplary embodiments, reference may be first had to FIGS. 1 and 2.

FIG. 1 is a system block diagram of a conventional gas sensing device 10. The gas sensing device 10 may comprise a printed circuit board (PCB) 100 providing mechanical support and electrical connections for:

a MEMS gas sensor circuit 102, e.g., a metal oxide gas sensor;

a microcontroller 104 configured to:

control operation of the MEMS gas sensor circuit 102 by sending (e.g., via digital communication such as I2C, SPI or the like) one or more control signals thereto, receive one or more output signals from the MEMS gas sensor circuit 102, and process said one or more output signals for checking the operation state of the MEMS gas sensor circuit 102; and additional circuitry 106 (e.g., a set of integrated circuits, IC) coupled to the microcontroller circuit 104 to provide various functions to the gas sensing device 10 such as connectivity to external devices, power management and the like.

The device available with companies of the STMicroelectronics group under the trade designation GHT25S is exemplary of a MEMS gas sensor circuit 102 suitable for use in one or more embodiments.

In particular, the MEMS gas sensor circuit 102 may comprise at least one semiconductor die which hosts:

a MEMS membrane (e.g., a micro-hotplate) hosting a heating system, typically, a resistor configured to be traversed by a current, and a gas sensing element, typically, a metal oxide layer whose resistance value is indicative of concentration of a certain target gas, and an application-specific integrated circuit (ASIC) comprising analog front end circuitry for interfacing with the heating system (to control heating of the MEMS membrane) and the sensing element (to sense the resistance value thereof), digital front end circuitry for interfacing with circuits external to the MEMS gas sensor circuit 102 (e.g., the microcontroller 104), and possibly other sensors such as a humidity sensor and/or a temperature sensor.

A gas sensing device 10 may be used in various applications to detect the concentration of a certain gas, e.g., a volatile organic compound such as carbon monoxide, carbon dioxide, methane and the like, as an indicator of possible failure of a system or component, for instance in a medical or industrial tool or equipment, or also in consumer electronics goods. An alert signal may be issued by the gas sensing device 10 as a result of said concentration detected by the MEMS gas sensor circuit 102 reaching a threshold value.

FIG. 2 is a flow diagram of an example possible operation flow on a conventional gas sensing device 10 which does not implement any self-diagnosis procedure.

As shown in FIG. 2, after a start step 200, which may correspond, for instance, to the start-up of the gas sensing device 10, the operation flow of the gas sensing device 10 may comprise:

at a step 202, receiving at the microcontroller 104 a signal, e.g., digital signal, from the MEMS gas sensor circuit 102, said signal being indicative of a value of resistance of the metal oxide gas sensing element;

at a step 204, processing in the microcontroller 104 said signal received from the MEMS gas sensor circuit 102 to compute a value of gas concentration as a function of one or more calibration functions (e.g., calibration maps, look-up tables, analytical functions) stored in a memory accessible by the microcontroller 104;

at a step 206, comparing the computed gas concentration value to a threshold value, to determine whether an alert signal should be issued or not; and as a result of a negative outcome (N) of step 206, resuming operation from step 202;

as a result of a positive outcome (Y) of step 206, issuing an alert signal at step 208, e.g., via a connectivity circuit module comprised in the circuitry 106.

The calibration function(s) of the gas sensing device 10 may be generated at the manufacturing level of the MEMS gas sensor circuit 102 and stored in a dedicated memory area (e.g., provided on the printed circuit board 100). Such memory area may be of a re-writable type, insofar as re-calibration of the MEMS gas sensor circuit 102 may be performed via software by modifying the calibration function(s).

It is noted that, depending on the application, in various embodiments an alert signal may be issued as a result of the computed gas concentration being higher than a first threshold (e.g., in case the gas sensor is used to detect flammable gases whose high concentration may be hazardous) or lower than a second threshold (e.g., in case the gas sensor is used in a medical device to detect oxygen concentration which should not fall below a certain limit).

Figure 3A:
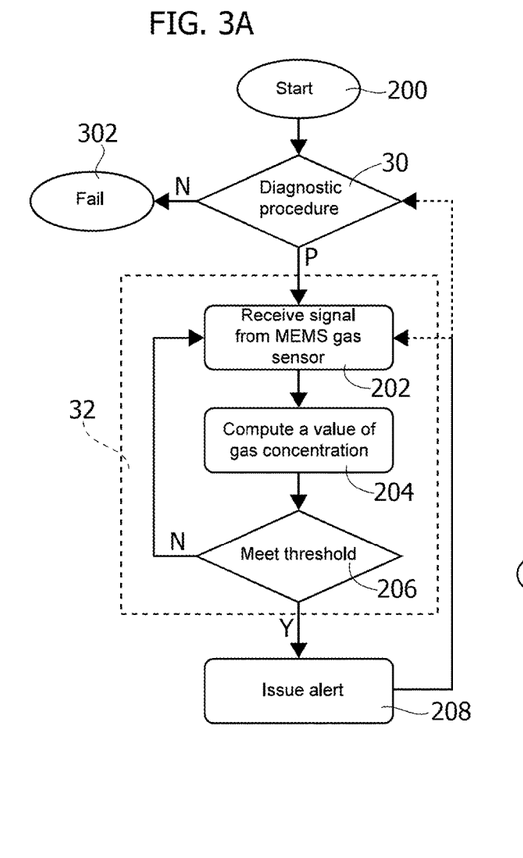
FIGS. 3A and 3B are block diagrams of example methods of operating a gas sensing device according to one or more embodiments.
Figure 3B:
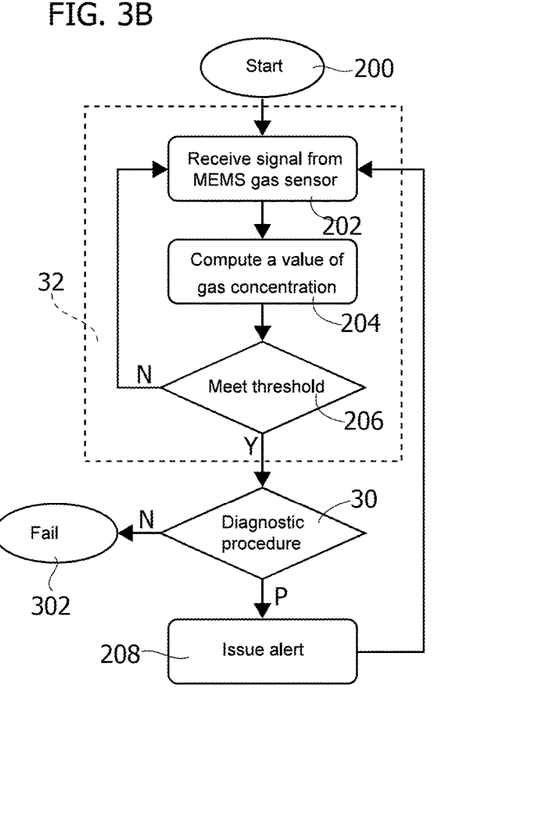

One or more embodiments as shown in the block diagrams of FIGS. 3A and 3B may provide a method of operating a gas sensing device 10 which comprises performing a diagnosis procedure to verify the operation state of the MEMS gas sensor circuit 102 before issuing an alert signal.

In particular, the operation flow shown in FIG. 3A may comprise, after a start step 200, performing a diagnostic procedure 30 of the MEMS gas sensor circuit 102. As a result of a negative outcome (N) of such diagnostic procedure 30, e.g., in case the MEMS gas sensor circuit 102 is found out to be faulty or damaged, the operation flow terminates at a step 302 in a "fail" mode and flags the MEMS gas sensor circuit 102 as damaged. Conversely, as a result of a positive outcome (P) of the diagnostic procedure 30, e.g., in case the MEMS gas sensor circuit 102 is found to be operating properly (e.g., within specifications), the operation flow proceeds with steps 202, 204, 206 and possibly 208 as described with reference to FIG. 2, with steps 202, 204 and 206 corresponding to a repeatable "main execution thread" 32 of the gas sensing device 10. After step 208, operation may resume either from step 30 (e.g., the diagnostic procedure 30 may be repeated after each alert signal issued) of from step 202 (e.g., the diagnostic procedure 30 is performed only once at start-up of the gas sensing device 10).

Alternatively, an operation flow as shown in FIG. 3B may comprise, after a start step 200, performing the main execution thread 32 of the gas sensing device 10, e.g., steps 202, 204 and 206. As a result of a positive outcome (Y) of step 206, e.g., in case an alert signal is to be issued, the operation flow may comprise performing the diagnostic procedure 30 of the MEMS gas sensor circuit 102. As a result of a negative outcome (N) of such diagnostic procedure 30, the operation flow terminates at a step 302 in a "fail" mode by flagging the MEMS gas sensor circuit 102 as damaged. Conversely, as a result of a positive outcome (P) of the diagnostic procedure 30, the operation flow proceeds with step 208 issuing an alert signal. After step 208, operation may resume from step 202.

Thus, some embodiments may comprise performing the diagnostic procedure 30 after the start step 200 (e.g., at start-up of the gas sensing device 10 and/or after issuing an alert signal), and other embodiments may comprise performing the diagnostic procedure 30 upon a positive outcome of the step 206 (e.g., before issuing an alert signal).

Further embodiments (whose operation flow is not illustrated in the drawings annexed herein for the sake of brevity only) may comprise performing the diagnostic procedure 30 both after the start step 200 and upon a positive outcome of the step 206, e.g., to increase robustness of the diagnosis feature. Still further embodiments may comprise performing the diagnostic procedure 30 periodically during operation of the gas sensing device 10 (e.g., every N executions of the main thread 32, with N being an arbitrary integer value possibly configurable by the user, or at regular time intervals).

Figure 4:
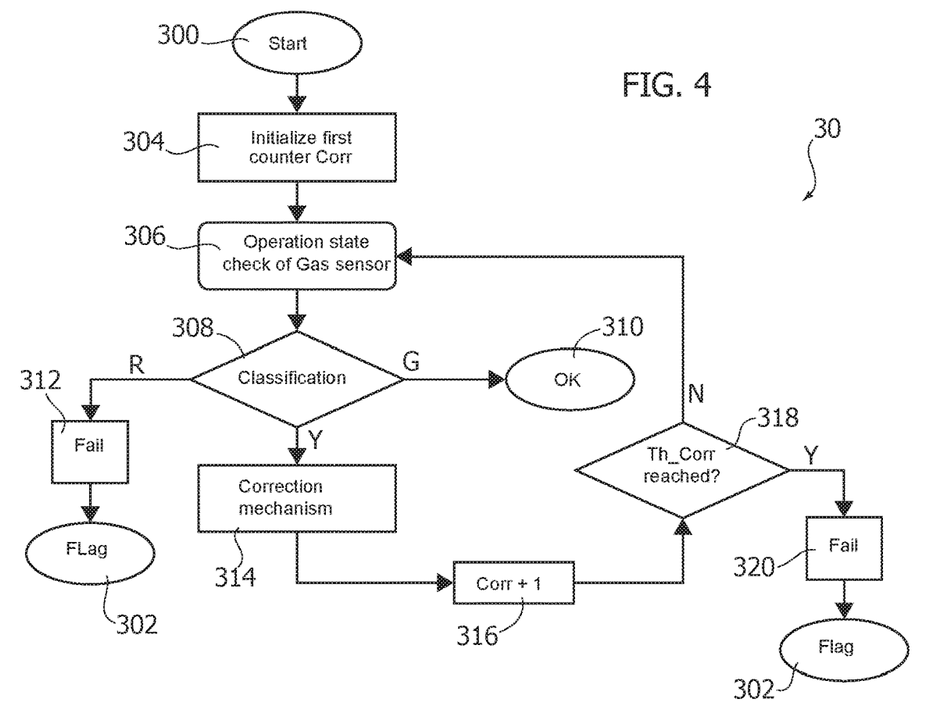
FIG. 4 is a block diagram of the example operation flow of a diagnostic procedure of a gas sensor in one or more embodiments.

FIG. 4 is a block diagram of an example operation flow of a diagnostic procedure 30 in one or more embodiments. In some embodiments, the diagnostic procedure is controlled by the microcontroller 104.

A diagnostic procedure 30 as shown in FIG. 4 may comprise the following steps:
300: start diagnostic procedure;
304: initialize a first counter Corr (e.g., set Corr=0);
306: perform an operation state check procedure of the MEMS gas sensor circuit 102, as further described in the following, thereby computing a set of parameters indicative of the operation state of the MEMS gas sensor circuit 102;
308: as a function of the value(s) of said set of parameters computed at step 306, classify the MEMS gas sensor circuit 102 as:
faulty/damaged (outcome R of block 308),
degraded (outcome Y of block 308), or
correctly operating (outcome G of block 308);
310: as a result of the MEMS gas sensor circuit 102 being found to be correctly operating, terminate the diagnostic procedure 30 with status "OK" and proceed with the normal operation flow of the gas sensing device 10 (e.g., proceed with step 202 according to FIG. 3A or with step 208 according to FIG. 3B: positive outcome P of the diagnostic procedure 30);
312: as a result of the MEMS gas sensor circuit 102 being found to be faulty/damaged, issue a fault signal and terminate the diagnostic procedure 30 in a "fail" mode with step 302 flagging the MEMS gas sensor circuit 102 as damaged (negative outcome N of the diagnostic procedure 30);
314: as a result of the MEMS gas sensor circuit 102 being found to be degraded, trigger a correction mechanism for compensating the sensitivity degradation and/or the response time degradation of the MEMS gas sensor circuit 102;
316: increase the value of the first counter Corr (e.g., set Corr=Corr+1);
318: check whether the current value of the first counter Corr has reached a threshold value Th_Corr;
as a result of a negative outcome (N) of step 318, continue operation from step 306, e.g., repeat the operation state check procedure after correction;
320: as a result of a positive outcome (Y) of step 318, issue a fault signal and terminate the diagnostic procedure 30 in a "fail" mode with step 302 flagging the MEMS gas sensor circuit 102 as damaged (negative outcome N of the diagnostic procedure 30).

In particular, the correction mechanism triggered at step 314 may comprise increasing by a determined threshold value the driving current of the heating resistor in the MEMS gas sensor circuit 102, thereby increasing the temperature of the MEMS micro-hotplate hosting the sensing element of the gas sensor (e.g., a metal oxide layer).

Of course, the detailed operation flow illustrated in FIG. 4 is purely an example and may change according to different embodiments. For instance, the checking act 318 may be performed directly after the classification step 308 in case of outcome Y of the classification step 308, with the steps 314 and/or 316 possibly performed only upon negative outcome (N) of step 318.

Thus, a diagnostic procedure 30 as shown in FIG. 4 may terminate with two possible outcomes (as shown also in FIGS. 3A and 3B), namely:
the MEMS gas sensor circuit 102 is eventually classified as "correctly operating", either at the first execution of the operation state check procedure 306 or after executing a limited number, e.g., lower than Th_Corr, of correction loops and subsequent operation state check procedures 306; or the MEMS gas sensor circuit 102 is eventually classified as "faulty/damaged", either after execution of a operation state check procedure 306 or because the correction mechanism was triggered more than Th_Corr times.

Figure 5:
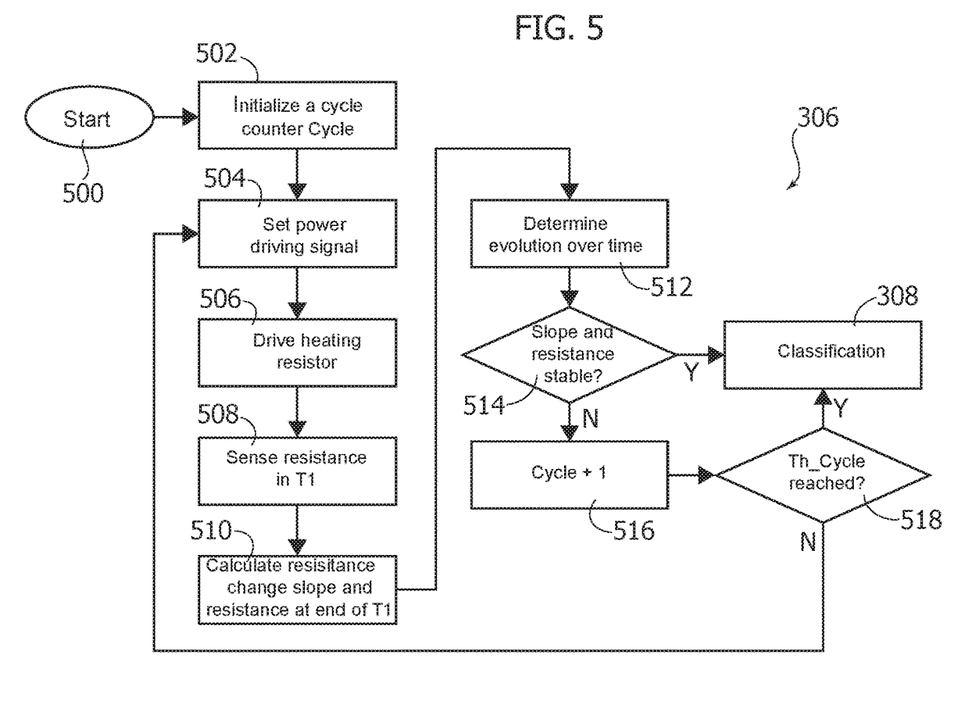
FIG. 5 is a block diagram of the example operation flow of an operation state check procedure of a gas sensor in one or more embodiments.

FIG. 5 is a block diagram exemplary of the operation flow of an operation state check procedure 306 in one or more embodiments. The operation state check procedure 306 may be performed, for example, as a state machine running in the MEMS gas sensor circuit 102 or by a microcontroller 104 coupled to the MEMS gas sensor circuit 102.

Figure 6:
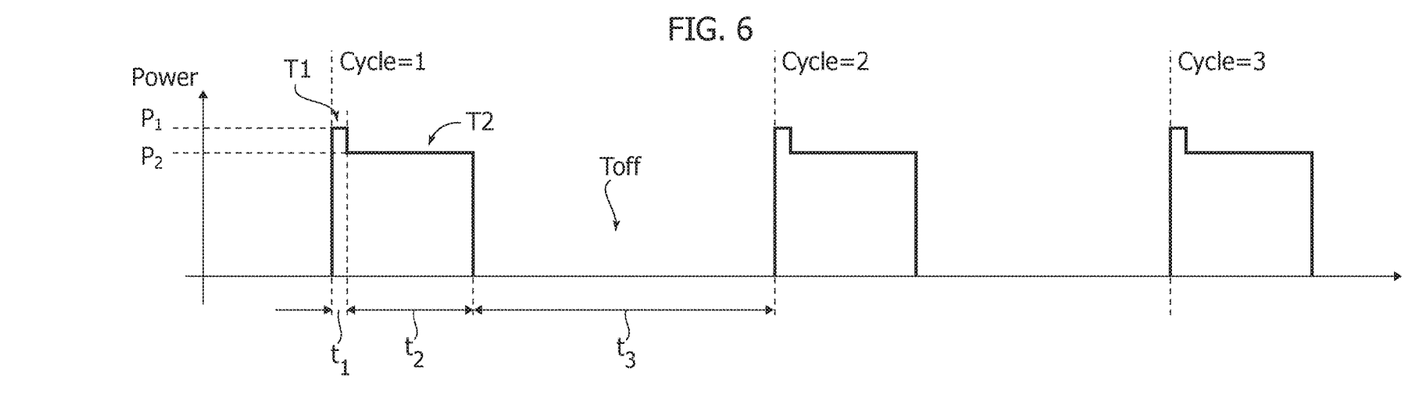
FIG. 6 is an example of a current driving signal for a heating resistor in a gas sensor in one or more embodiments.

An operation state check procedure 306 as shown in FIG. 5 may comprise the following steps:
- 500: start operation state check procedure;
- 502: initialize a cycle counter Cycle (e.g., set Cycle=1);
- 504: set a power driving signal (e.g., a current signal) for the heating resistor in the MEMS gas sensor circuit 102, e.g., as shown in FIG. 6;
- 506: start driving of the heating resistor;
- 508: sense, during time interval T1 of the driving signal, a signal Rs(t) indicative of the resistance of the gas sensing element in the MEMS gas sensor circuit 102;
- 510: calculate, as a function of said resistance signal sensed during time interval T1, a respective value of slope of the signal Rs(t) (e.g., the average slope of signal Rs(t) over the time interval T1) and a respective value of resistance $Rs(t_1)$, e.g., the value of the signal Rs(t) at the end of the time interval T1;
- 512: process the current calculated values of slope of the resistance signal Rs(t) and resistance $Rs(t_1)$ to determine a measure of evolution over time of the slope of the resistance signal Rs(t) and resistance $Rs(t_1)$;
- 514: check whether slope of the resistance signal Rs(t) and resistance $Rs(t_1)$ are in a steady state condition compared to previous values thereof;
- as a result of a positive outcome (Y) of act 514, continue with step 308 (e.g., as a function of values of slope of the resistance signal Rs(t) and resistance $Rs(t_1)$, classify the MEMS gas sensor circuit 102 as faulty/damaged, degraded or correctly operating);
- 516: a result of a negative outcome (N) of act 514, increase the value of the cycle counter Cycle (e.g., set Cycle=Cycle+1);
- 518: check whether the current value of the cycle counter Cycle has reached a threshold value Th_Cycle;
- as a result of a negative outcome (N) of step 518, continue operation from step 504;
- as a result of a positive outcome (Y) of step 518, continue with step 308.

FIG. 6 is an example power driving signal for the heating resistor in the MEMS gas sensor circuit 102 (e.g., a signal indicative of a current provided to the heating resistor) as may be applied in one or more embodiments during an operation state check procedure 306. In particular, at each cycle comprising steps 504 to 518, the driving signal provided to the heating resistor may comprise:
- a first section T1 having duration $t_1$ (e.g., 0.5 seconds) wherein the heating resistor is supplied with a power P1 (e.g., with a current having a first value $I_1$),
- a second section T2 having duration $t_2$ (e.g., 1 second) wherein the heating resistor is supplied with a power P2 (e.g., with a current having a second value $I_2$, e.g., lower than $I_1$), with duration $t_2$ optionally being higher than $t_1$, and
- a third section Toff having duration $t_3$ (e.g., 3.5 seconds) wherein the heating resistor is not supplied with current (e.g., it is off), with duration $t_3$ optionally being higher than $t_1$ and/or $t_2$, in some embodiments with $t_3 \gg t_1$ and $t_3 \gg t_2$ for enhancing the slope trend of the resistance signal sensed during the first section T1 with duration $t_1$.

Figures 7A, 7B, 7C:
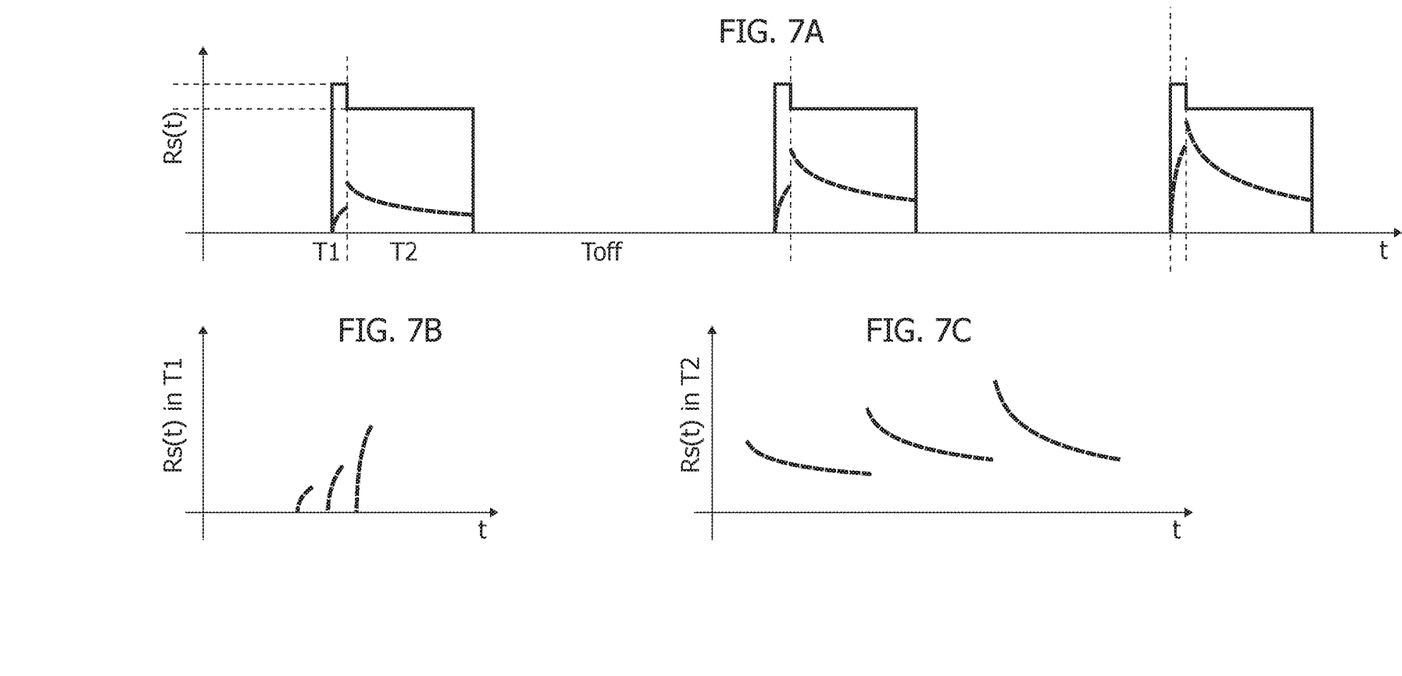
FIGS. 7A, 7B and 7C are examples of possible behavior over time of a gas sensor response in one or more embodiments.

FIGS. 7A, 7B and 7C are examples of possible behaviors over time of the MEMS gas sensor response during an operation state check procedure 306 in one or more embodiments. In particular, FIG. 7A shows the time behavior of the sensed signal Rs(t) (illustrated with dashed line) during the intervals T1, T2 and Toff of the driving signal of the heating resistor (illustrated with solid line); FIGS. 7B and 7C exemplify with greater detail the time behavior of the sensed signal Rs(t) during the intervals T1 and T2, respectively. It is therefore illustrated that the average slope and the final value of the signal Rs(t) during interval T1 of subsequent cycles may tend to a steady state condition after a determined threshold number of cycles.

In one or more embodiments, the step 512 of processing the current calculated values of slope of the resistance signal Rs(t) and resistance $Rs(t_1)$ may comprise, for instance, determining phase and magnitude of a vector in a polar diagram, said vector having components <$Rs(t_1)$, slope(Rs(t))>.

Therefore, in one or more embodiments the checking act 514 may comprise, for instance, checking whether said phase and magnitude are approximately constant with respect to a previous cycle of the operation state check procedure 306. In some embodiments, the checking act 514 may comprise:
- computing a settlement index as a function of the distance between the point of coordinates <$Rs(t_1)$, slope(Rs(t))> of the actual cycle and the point of coordinates <$Rs(t_1)$, slope(Rs(t))> of the previous cycle, and
- comparing said settlement index with a determined threshold, and detecting a steady state condition as a result of the settlement index being lower than the threshold. The threshold may have a determined value, which may be predetermined.

In one or more embodiments, the step 308 of classifying the MEMS gas sensor circuit 102 as faulty/damaged, degraded or correctly operating as a function of the values of the set of parameters computed with a operation state check procedure 306 (e.g., $Rs(t_1)$ and slope of Rs(t) during T1) may comprise analyzing the trajectory and/or the final point reached by the vector having components <$Rs(t_1)$, slope(Rs(t))> in a polar diagram.

For instance, in one or more embodiments the step 308 may comprise classifying the MEMS gas sensor circuit 102 as a function of the phase of the final vector having components <$Rs(t_1)$, slope(Rs(t))>. Purely by way of example, the sensor may be classified as:
- "good", if said phase is between 40° and 60°,
- "medium", if said phase is between 20° and 40°,
- "poor", if said phase is between 0° and 20°, and
- "fail", if said phase is less than 0°.

Of course, such values are purely exemplary and may be changed, e.g., depending on the type of MEMS gas sensor circuit 102.

Figure 8:
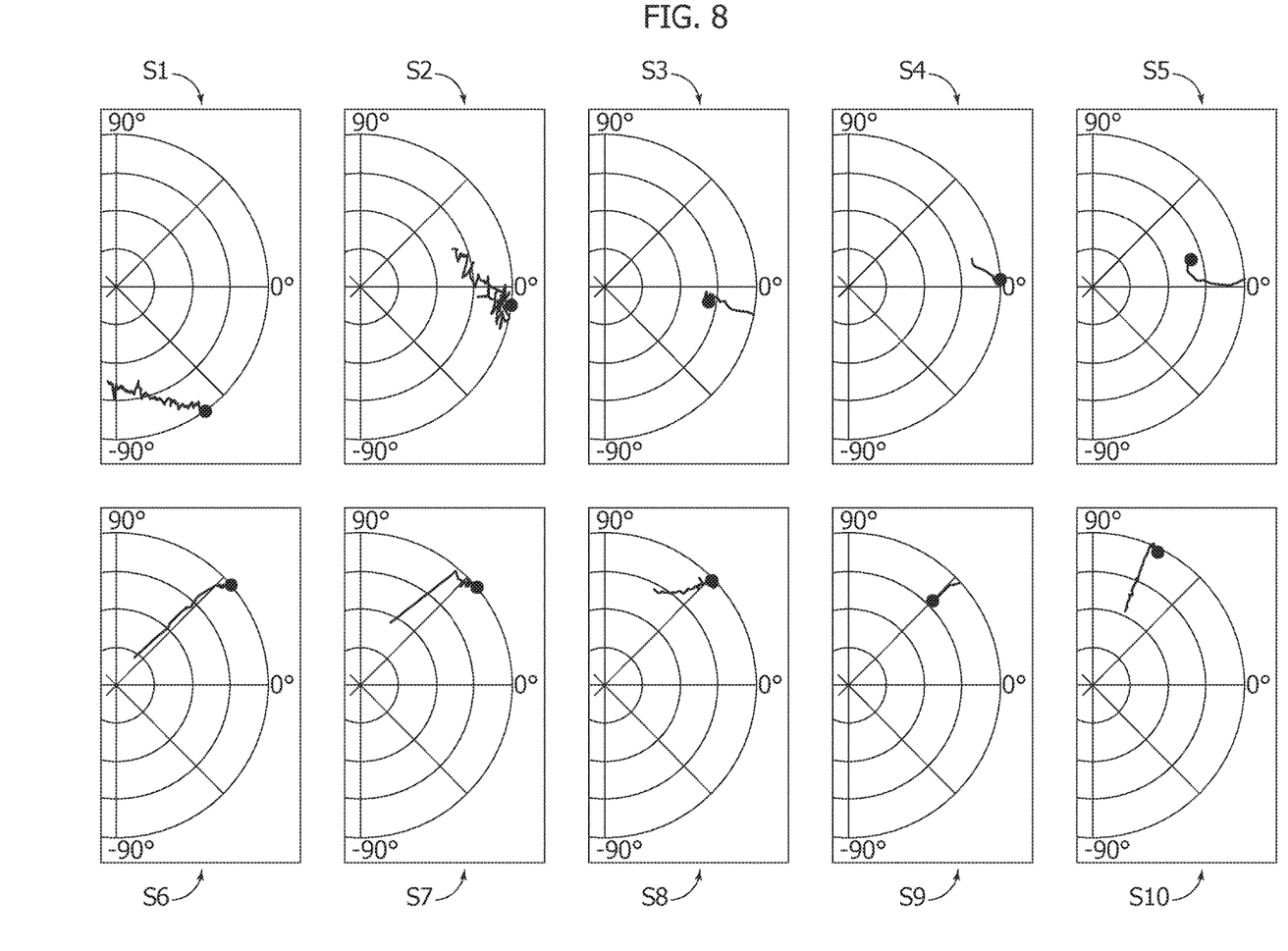
FIG. 8 is an example of possible signal processing in one or more embodiments.

FIG. 8 is an example of different trajectories of the vector having components <$Rs(t_1)$, slope(Rs(t))> as sensed during an operation state check procedure 306 of respective different gas sensors S1 to S10. The following table illustrates the value of the phase of the respective vectors having components <$Rs(t_1)$, slope(Rs(t))> once in steady state condition, and the corresponding sensitivity of the respective gas sensor:

| Sensor No. | Phase at steady state | Sensitivity |
|---|---|---|
| S1 | −54.4° | 0 |
| S2 | −7.7° | 0 |
| S3 | −4.8° | 0 |
| S4 | 1.6° | 1.11 |
| S5 | 15.7° | 1.33 |
| S6 | 40.9° | 1.43 |
| S7 | 42.6° | 1.50 |
| S8 | 44.5° | 1.57 |
| S9 | 45.1° | 1.63 |
| S10 | 64.1° | 1.33 |

As shown in the table above, the phase of the vector having components <Rs(t$_1$), slope(Rs(t))> at steady state, and/or the trajectory followed by said vector in the polar plane during the operation state check procedure 306, may be indicative of the performance of the MEMS gas sensor circuit 102. For instance, sensors S1 to S3 may be classified as faulty/damaged (e.g., having a bad operation state), sensors S4 and S5 may be classified as degraded (e.g., having a medium operation state) and sensors S6 to S10 may be classified as correctly operating (e.g., having a good operation state).

In one or more embodiments, the diagnostic procedure 30 may be run by the MEMS gas sensor circuit 102 (e.g., by means of an internal state machine) at power-on and/or periodically, and the main execution thread of the microcontroller 104 may be interrupted as a result of the diagnostic procedure 30 terminating with outcome "MEMS gas sensor circuit 102 classified as faulty/damaged".

Advantageously over known solutions, one or more embodiments may not involve interrupting or stopping the operation of the tool or equipment where the gas sensing device 10 is installed for performing the diagnostic procedure 30, insofar as the diagnostic procedure 30 may be carried out independently from the current operating conditions of the tool or equipment where the gas sensing device 10 is installed (e.g., the diagnostic procedure 30 may not involve operating the gas sensing device 10 in a controlled environment or under controlled test conditions).

As shown herein, a gas sensing device (e.g., 10) may comprise:
a gas sensor circuit (e.g., 102) comprising a resistive gas sensing element, and
a control circuit (e.g., 104) coupled to the gas sensor circuit.

As shown herein, a method of operating a gas sensing device may comprise:
receiving (e.g., 202) at the control circuit a signal from the gas sensor circuit, said signal being indicative of a value of resistance of said resistive gas sensing element;
processing (e.g., 204) said signal received from the gas sensor circuit to compute a value of a gas concentration (e.g., as a function of at least one calibration map);
performing a comparison (e.g., 206) of said value of gas concentration to a threshold value and setting the gas sensing device to an alert signal issue state (e.g., 208) as a function of the outcome of said comparison, wherein setting the gas sensing device to said alert signal issue state is conditioned on the outcome of a diagnosis procedure (e.g., 30).

As shown herein, the diagnosis procedure may comprise:
computing (e.g., 306) a set of parameters indicative of the state (e.g., operation state) of the gas sensor circuit;
classifying (e.g., 308) the gas sensor circuit as a function of the parameters in said set of parameters computed, in one of a first class, a second class and a third class indicative of the gas sensor circuit being faulty, degraded or correctly operating, respectively; and
i) as a result of the gas sensor circuit being classified in said first class, disabling (e.g., 302) setting the gas sensing device to said alert signal issue state;
ii) as a result of the gas sensor circuit being classified in said second class, triggering a sensitivity correction procedure (e.g., 314) of the gas sensor circuit and repeating said diagnosis procedure; and
iii) as a result of the gas sensor circuit being classified in said third class, enabling setting the gas sensing device to said alert signal issue state.

As shown herein, a method may comprise, as a result of the gas sensor circuit being classified in said first class, issuing a sensor fault signal.

As shown herein, the gas sensor circuit may comprise a resistive heater, and the sensitivity correction procedure may comprise increasing the driving current of said resistive heater.

As shown herein, performing said diagnosis procedure may comprise:
counting (e.g., 316) a number of consecutive executions of said sensitivity correction procedure, and
classifying the gas sensor circuit in said first class as a result of said number of consecutive executions of said sensitivity correction procedure being higher than a threshold value.

As shown herein, said computing a set of parameters indicative of the state of the gas sensor circuit may comprise checking whether the parameters in said set of parameters are in a steady state condition, and repeating said computing as a result of said parameters in said set of parameters failing to be in a steady state condition.

As shown herein, classifying the gas sensor circuit as a function of parameters in said set of computed parameters may comprise analyzing time evolution patterns and/or final values reached by the parameters in said set of computed parameters.

As shown herein, the gas sensor circuit may comprise a resistive heater, and computing a set of parameters indicative of the state of the gas sensor circuit may comprise:
applying a current pulse (e.g., $I_1$, $I_2$) to said resistive heater,
sensing said signal received from the gas sensor circuit as a result of application of said current pulse, and
computing, as a function of said signal received, a value of resistance of said resistive gas sensing element and a value of slope of said signal received.

As shown herein, the current pulse applied to the resistive heater may comprise:
a first portion having a first duration (e.g., $t_1$) wherein said current pulse has a first current value (e.g., $I_1$),
a second portion having a second duration (e.g., $t_2$) wherein said current pulse has a second current value (e.g., $I_2$) different from said first current value, and
a third portion having a third duration (e.g., $t_3$) wherein no current is applied to the resistive heater.

As shown herein, the first current value may be higher than the second current value and the third duration may be higher than the first duration and the second duration.

As shown herein, a method may comprise performing said diagnosis procedure at power-up of the gas sensing device.

As shown herein, a method may comprise performing said diagnosis procedure after each alert signal issued.

As shown herein, a method may comprise performing said diagnosis procedure periodically.

As shown herein, a gas sensing device may comprise a gas sensor circuit comprising a resistive gas sensing element, and a control circuit coupled to the gas sensor circuit, wherein the gas sensing device is configured to operate according to the method of one or more embodiments.

The disclosed techniques may have various technical and commercial advantages. For example, because the MEMS gas sensor and the ASIC coupled thereto have dedicated designs, the gas sensor is simplified and has a reduced size. Resultantly, the manufacturing cost is also reduced.

The diagnosis of the gas sensor does not require that the gas sensor be operated under any controlled conditions, e.g., in a controlled environment, which is desirable for at least some of the application scenarios of the gas sensor. For example, in some application scenarios, it may not be possible to stop the equipment or production tools where the gas sensors are installed in order to run a sensor self-diagnosis procedure under the otherwise requested controlled conditions. For another example, the gas sensors can be placed in a location which is not easily accessible and the diagnosis still can be performed. Further, there is no need for a reference instrument to be placed in a same environmental condition as the gas sensor to be tested.

Without prejudice to the underlying principles, the details and embodiments may vary, even significantly, with respect to what has been described by way of example only, without departing from the extent of protection.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of operating a gas sensing device, the method comprising:
   receiving a first signal from a gas sensor circuit having a resistive gas sensing element, the first signal being indicative of a resistance value of the resistive gas sensing element;
   processing the first signal to compute a value of a gas concentration;
   comparing the value of gas concentration to a threshold value; and
   setting the gas sensing device to an alert signal issue state based on an outcome of the comparing, wherein the setting the gas sensing device to the alert signal issue state includes a diagnosis procedure, the diagnosis procedure including:
      computing a set of parameters indicative of a state of the gas sensor circuit;
      classifying the gas sensor circuit, based on values of the parameters in the set of parameters computed, in one of a first class, a second class and a third class indicative of the gas sensor circuit being faulty, degraded, or correctly operating, respectively; and
      in response to the gas sensor circuit being classified in the first class, disabling the setting the gas sensing device to the alert signal issue state;
      in response to the gas sensor circuit being classified in the second class, triggering a sensitivity correction procedure of the gas sensor circuit;
      in response to the gas sensor circuit being classified in the third class, enabling setting the gas sensing device to the alert signal issue state; and
   counting a number of consecutive executions of the sensitivity correction procedure.

2. The method of claim 1, comprising, as a result of the gas sensor circuit being classified in the first class, issuing a sensor fault signal.

3. The method of claim 1, wherein the gas sensor circuit comprises a resistive heater, and wherein the sensitivity correction procedure comprises increasing a power supplied to the resistive heater.

4. The method of claim 1, wherein the computing the set of parameters comprises determining whether the values of the parameters in the set of parameters are in a steady state condition, and repeating the computing in response to the values of the parameters in the set of parameters failing to be in a steady state condition.

5. The method of claim 4, wherein the classifying the gas sensor circuit based on the values of the parameters in the set of parameters comprises analyzing one or more of a time evolution pattern or a final value reached by a parameter in the set of parameters.

6. The method of claim 1, wherein the gas sensor circuit comprises a resistive heater, and wherein the computing the set of parameters comprises:
   applying a current pulse to the resistive heater;
   sensing a second signal from the gas sensor circuit in response to the application of the current pulse; and
   computing, based on the second signal, a value of resistance of the resistive gas sensing element and a value of a slope of the second signal received.

7. The method of claim 6, wherein the current pulse applied to the resistive heater comprises:
   a first portion having a first duration and a first current value;
   a second portion having a second duration and a second current value different from the first current value; and
   a third portion having a third duration and zero current value.

8. The method of claim 7, wherein the first current value is higher than the second current value and the third duration is larger than each one of the first duration or the second duration.

9. The method of claim 1, comprising performing the diagnosis procedure at power-up of the gas sensing device.

10. The method of claim 1, comprising performing the diagnosis procedure after an alert signal has been issued.

11. The method of claim 1, comprising performing the diagnosis procedure periodically.

12. A gas sensing device, comprising:
   a gas sensor circuit comprising a resistive gas sensing element;
   a control circuit coupled to the gas sensor circuit, the control circuit operable to control the gas sensor circuit by:
      applying a first signal on the gas sensor circuit;
      detecting a change of resistive value of the resistive gas sensing element in response to the first signal;
      determining an operation state of the gas sensor circuit based on the change of resistive value; and triggering a sensitivity correction procedure of the gas sensor circuit based on the operation state of the gas sensor circuit; and disabling the gas sensing device to issue an alert signal according to a measurement result of the gas sensor circuit.

13. The gas sensing device of claim 12, wherein the control circuit is operable to control the gas sensor circuit based on the operation state of the gas sensor circuit by:

enabling the gas sensing device to issue the alert signal according to the measurement result of the gas sensor circuit.

14. The gas sensing device of claim 12, wherein the gas sensor circuit comprises a resistive heater, and wherein the applying a first signal on the gas sensor circuit includes applying a current pulse to the resistive heater.

15. The gas sensing device of claim 14, wherein the detecting the change of resistive value of the resistive sensing element includes:

sensing a second signal from the gas sensor circuit in response to the application of the current pulse; and
computing, based on the second signal, a resistance value of the resistive gas sensing element and a slope of the change of the resistive value.

16. The gas sensing device of claim 14, wherein the current pulse includes:

a first portion having a first duration and a first current value;
a second portion having a second duration and a second current value different from the first current value; and
a third portion having a third duration and zero current value.

17. The gas sensing device of claim 16, wherein the first current value is higher than the second current value and the third duration is larger than each one of the first duration or the second duration.

18. A method, comprising:

applying a current pulse on a MEMS gas sensor circuit having a resistive sensing element, the current pulse having a first stage and a second stage of different durations and different current values;
detecting a change of resistive value of the resistive sensing element in response to the current pulse;
determining a set of characteristics of the change of resistive value; and
determining an operation state of the gas sensor circuit based on the set of characteristics; and
disabling the gas sensor circuit to issue an alert signal according to a measurement result of the gas sensor circuit.

19. The method of claim 18, wherein the set of characteristics include a time evolution pattern of the change of resistive value of the resistive sensing element at an end of the current pulse.

20. A method of operating a gas sensing device, wherein the gas sensing device comprises:

a gas sensor circuit comprising a resistive gas sensing element; and
a control circuit coupled to the gas sensor circuit,
the method comprising:

receiving at the control circuit a signal from the gas sensor circuit, the signal being indicative of a value of resistance of the resistive gas sensing element;
processing the signal received from the gas sensor circuit to compute a value of a gas concentration; and
performing a comparison of the value of gas concentration to a certain threshold value and setting the gas sensing device to an alert signal issue state as a function of an outcome of the comparison, wherein setting the gas sensing device to the alert signal issue state is conditioned on an outcome of a diagnosis procedure, the diagnosis procedure comprising:

computing a set of parameters indicative of a state of the gas sensor circuit;
classifying the gas sensor circuit as a function of the parameters in the set of parameters computed, in one of a first class, a second class and a third class indicative of the gas sensor circuit being faulty, degraded or correctly operating, respectively; and
i) as a result of the gas sensor circuit being classified in the first class, disabling setting the gas sensing device to the alert signal issue state;
ii) as a result of the gas sensor circuit being classified in the second class, triggering a sensitivity correction procedure of the gas sensor circuit and repeating the diagnosis procedure; and
iii) as a result of the gas sensor circuit being classified in the third class, enabling setting the gas sensing device to the alert signal issue state;

wherein the gas sensor circuit includes a resistive heater, and wherein computing the set of parameters indicative of the state of the gas sensor circuit comprises:

applying a current pulse to the resistive heater;
sensing the signal received from the gas sensor circuit as a result of application of the current pulse; and
computing, as a function of the signal received, a value of resistance of the resistive gas sensing element and a value of slope of the signal received.

21. The method of claim 20, wherein the diagnosis procedure comprises:

counting a number of consecutive executions of the sensitivity correction procedure; and
classifying the gas sensor circuit in the first class as a result of the number of consecutive executions of the sensitivity correction procedure being higher than a threshold.

* * * * *